United States Patent [19]

Tagami et al.

[11] Patent Number: 5,453,524

[45] Date of Patent: Sep. 26, 1995

[54] PHOSPHORUS-CONTAINING ISOPRENOID DERIVATIVES

[75] Inventors: Katsuya Tagami; Ichirou Yoshida; Naoki Kobayashi; Yoshio Fukuda; Yoshihito Eguchi; Makoto Nakagawa; Hironobu Hiyoshi; Hironori Ikuta; Makoto Kaino; Kenji Hayashi; Issei Ohtsuka; Shinya Abe; Shigeru Souda, all of Ibaraki, Japan

[73] Assignee: Eisai Co., Ltd., Tokyo, Japan

[21] Appl. No.: 199,231

[22] PCT Filed: Aug. 27, 1992

[86] PCT No.: PCT/JP92/01082

§ 371 Date: Feb. 22, 1994

§ 102(e) Date: Feb. 22, 1994

[87] PCT Pub. No.: WO93/04073

PCT Pub. Date: Mar. 4, 1993

[30] Foreign Application Priority Data

Aug. 27, 1991 [JP] Japan ................................... 3-215250
Dec. 4, 1991 [JP] Japan ................................... 3-319468

[51] Int. Cl.$^6$ .............................................. C07F 9/02
[52] U.S. Cl. ................... 551/78; 554/84; 558/166; 558/179; 558/182; 558/190; 558/155; 558/158; 558/161
[58] Field of Search ............... 554/78, 84; 558/155, 558/158, 161, 166, 179, 182, 190; 514/108, 136, 143

[56] References Cited

U.S. PATENT DOCUMENTS

5,157,027  10/1993  Biller et al. ........................... 514/107

FOREIGN PATENT DOCUMENTS

0324421  1/1989  European Pat. Off. .
0356866  8/1989  European Pat. Off. .
0513761  5/1992  European Pat. Off. .
0541037  11/1992  European Pat. Off. .

*Primary Examiner*—José G. Dees
*Assistant Examiner*—Deborah D. Carr
*Attorney, Agent, or Firm*—Flynn, Thiel, Boutell & Tanis

[57] ABSTRACT

The present invention provides a phosphorus-containing isoprenoid derivative represented by the following general formula (I) or a pharmacologically acceptable salt thereof, which is useful as a preventive and therapeutic agent for diseases for which a squalene synthetase inhibiting action is efficacious:

$$\text{(I)}$$

wherein $R^1$ and $R^2$ each represent a hydrogen atom, a lower alkyl, cycloalkyl, alkenyl or alkynyl group, an aryl group which may be substituted, an arylalkyl group in which the aryl group may be substituted, or a heteroaryl or heteroarylalkyl group; $R^3$ and $R^4$ each represent a hydrogen atom, a lower alkyl group or an alkali metal; Y represents a group represented by the formula:

(wherein $R^5$ and $R^6$ each represent a hydrogen atom, a lower alkyl group or an alkali metal or a group represented by the formula: —$CO_2R^7$ (wherein $R^7$ represents a hydrogen atom, a lower alkyl group or an alkali metal); Z represents a group represented by the Formula: —$(CH_2)_m$— (wherein m is an integer of 0 to 3), a group represented by the formula: —$(CH_2)_p$—CH=CH—$(CH_2)_q$— (wherein p is 0 or 1 and q is 1 or 2) or a group represented by the Formula:

$$-A-N(R^8)-(CH_2)_r-$$

(wherein $R^8$ represents a hydrogen atom or a lower alkyl group; A represents an alkylene chain which has 1 to 5 carbon atoms and which may have a substituent on each carbon atom; and r is zero or an integer of 1 to 5); and n is zero or an integer of 1 to 5.

8 Claims, No Drawings

PHOSPHORUS-CONTAINING ISOPRENOID DERIVATIVES

This application is a 371 of PCT/JP92/01082, filed Aug. 27, 1992.

FIELD OF INDUSTRIAL APPLICATION

The present invention relates to a novel phosphorus-containing isoprenoid derivative. More particularly, it relates to a phosphorus-containing isoprenoid derivative useful as a drug.

BACKGROUND OF THE INVENTION AND PRIOR ART

Ischemic heart diseases such as myocardial infarction still account for a high proportion of the death causes of the middle-aged and the elderly. Ischemic heart diseases are known to be induced by hyperlipemia which is a principal factor of atherosclerosis which is one of the adult diseases. Accordingly, the treatment of hyperlipemia which is a stage precedent to ischemic heart diseases such as myocardial infarction is essential, so that studies have been made for many years to develop an excellent hyperlipemia remedy.

Recently, an HMG-CoA reductase inhibitor has been developed as a hyperlipemia remedy and has been ascertained to have an excellent cholesterol level lowering activity. However, this inhibitor also hinders the biosynthesis of $CoQ_{10}$ or dolichol, so that there is a danger of causing an adverse effect such as cardiac hypofunction, muscle ache or infirmity. Meanwhile, a desmosterol reductase inhibitor has a disadvantage that serious adverse effects such as cataract are caused by the accumulation of desmosterol.

Under these circumstances, it is still eagerly expected to develop a hyperlipemia remedy which is free from the above adverse effects and exhibits an excellent cholesterol level lowering activity.

Under the above circumstances, the inventors of the present invention started studies to find a compound having an inhibitory activity against squalene synthetase, and have found that a phosphorus-containing isoprenoid derivative can attain the object. The present invention has been accomplished on the basis of this finding.

Although some phosphorus-containing hydrocarbon compounds useful as drugs are disclosed in Japanese Patent Laid-Open Nos. 56492/1990 and 188288/1990, they are different from the compounds of the present invention in both structure and efficacy as drugs. Further, some phosphorus-containing isoprenoid derivatives useful as drugs are also disclosed in Japanese Patent Laid-Open Nos. 101088/1990 and 285821/1990. However, these derivatives are different from those of the present invention in structure.

CONSTITUTION OF THE INVENTION

The present invention relates to a phosphorus-containing isoprenoid derivative represented by the following general formula (I) and pharmacologically acceptable salts thereof:

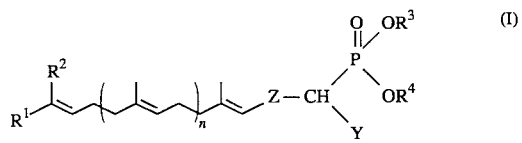

wherein $R^1$ and $R^2$ may be the same or different from each other and each represent a hydrogen atom, a lower alkyl, cycloalkyl, alkenyl or alkynyl group, an aryl group which may be substituted, an arylalkyl group in which the aryl group may be substituted, or a heteroaryl or heteroarylalkyl group;

$R^3$ and $R^4$ may be the same or different from each other and each represent a hydrogen atom, a lower alkyl group or an alkali metal;

Y represents a group represented by the formula:

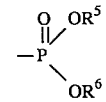

(wherein $R^5$ and $R^6$ may be the same or different from each other and each represent a hydrogen atom, a lower alkyl group or an alkali metal), or a group represented by the formula: $-CO_2R^7$ (wherein $R^7$ represents a hydrogen atom, a lower alkyl group or an alkali metal);

Z represents a group represented by the formula: $-(CH_2)_m-$ (wherein m is zero or an integer of 1 to 3), a group represented by the formula: $-(CH_2)_p-CH=CH-(CH_2)_q-$ (wherein p is 0 or 1 and q is 1 or 2) or a group represented by the formula:

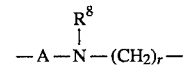

(wherein $R^8$ represents a hydrogen atom or a lower alkyl group; A represents an alkylene chain which has 1 to 5 carbon atoms and which may have a substituent on each carbon atom; and r is zero or an integer of 1 to 5); and n is zero or an integer of 1 to 5.

In the above definition of the compound (I) according to the present invention, the lower alkyl group defined with respect to $R^1$, $R^2$, $R^3$, $R^4$, $R^5$, $R^6$, $R^7$ and $R^8$ is a linear or branched alkyl group having 1 to 8 carbon atoms and examples thereof include methyl, ethyl, propyl, isopropyl, butyl, isobutyl, sec-butyl, tert-butyl, pentyl(amyl), isopentyl, neopentyl, tert-pentyl, 1-methylbutyl, 2-methylbutyl, 3-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl and octyl groups, among which methyl, ethyl, propyl and isopropyl groups are preferable, with methyl and ethyl groups being particularly preferable.

The cycloalkyl group defined with respect to $R^1$ and $R^2$ is one having 3 to 7 carbon atoms, preferably 3 to 6 carbon atoms. The cycloalkyl group may be substituted with a halogen atom, a lower alkyl or lower alkoxy group or the like.

The alkenyl group defined with respect to $R^1$ and $R^2$ may be one derived from any of the above lower alkyl groups, and examples thereof include ethylene, propylene, isopropylene and butylene groups, among which methylene and ethylene groups are preferable.

The alkenyl group defined with respect to $R^1$ and $R^2$ may be one derived from any of the above lower alkyl groups, an example thereof being an acetylene group.

The aryl group defined with respect to $R^1$ and $R^2$ includes phenyl and naphthyl groups. Further, the substituent on the aryl group includes a hydroxyl group, halogen atoms and lower alkyl, lower alkoxy, nitro and amino groups.

The aryl group constituting the arylalkyl group defined with respect to $R^1$ and $R^2$ includes phenyl and naphthyl groups, while the alkyl group (i.e., alkylene chain) constituting the arylalkyl group is one having 1 to 5 carbon atoms, preferably 1 to 3 carbon atoms. Further, the substituent on the aryl group includes a hydroxyl group, halogen atoms, and lower alkyl, lower alkoxy, nitro and amlno groups.

The heteroaryl group defined with respect to $R^1$ and $R^2$ is a 5- or 6-membered ring containing one or two atoms selected from among nitrogen, oxygen and sulfur atoms.

The heteroarylalkyl group defined with respect to $R^1$ and $R^2$ is one derived from the above heteroaryl group. The alkyl group (i.e., alkylene chain) constituting the heteroarylalkyl group is one having 1 to 5 carbon atoms, preferably 1 to 3 carbon atoms.

The alkali metal defined with respect to $R^3$, $R^4$, $R^5$, $R^6$ and $R^7$ includes lithium, sodium, potassium and rubidium, among which lithium, sodium and potassium are preferable, with sodium and potassium being still preferable.

A represents an alkylene chain having 1 to 5 carbon atoms, preferably 1 to 3 carbon atoms. The alkylene chain may have one or two substituents on each carbon atom and preferable examples of the substituents include lower alkyl groups.

m is zero or an integer of 1 to 3, preferably 0 or an integer of 1 to 2.

r is zero or an integer of 1 to 5, preferably 1 to 3.

n is zero or an integer of 1 to 5, preferably 1 to 3.

The pharmacologically acceptable salt according to the present invention includes inorganic acid salts such as hydrochloride, hydrobromide, sulfate and phosphate; organic acid salts such as acetate, maleate, tartrate, methanesulfonate, benzenesulfonate and toluenesulfonate; and amino acid salts such as arginimate, aspartate and glutamate.

Further, the derivative of the present invention may form a metal salt such as calcium or magnesium salt. The pharmacologically acceptable salt of the present invention includes these metal salts.

Although the compound of the present invention may be present as geometrical isomers (i.e., cis- and trans-isomers), the present invention includes both of the isomers.

Representative processes for preparing the compound of the present invention will now be described.

Preparation Process 1

When $R^3$, $R^4$, $R^5$, $R^6$ and $R^7$ are each a lower alkyl group, it can be prepared by the following process:

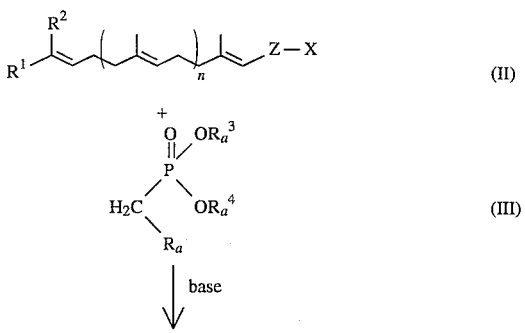

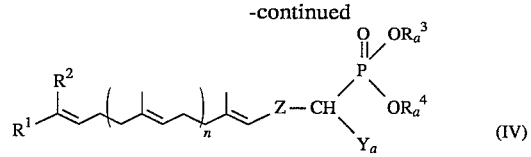

wherein $Y_a$ is a group represented by the formula:

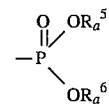

(wherein $R^5_a$ and $R^6_a$ may be the same or different from each other and each represent a lower alkyl group) or a group represented by the formula: $—CO_2R^7_a$ (wherein $R^7_a$ represents a lower alkyl group);

$R^3_a$ and $R^4_a$ may be the same or different from each other and each represent a lower alkyl group;

X represents a halogen atom or a methylsulfonyloxy or p-tolylsulfonyloxy group; and $R^1$, $R^2$, Z and n are each as defined above.

Specifically, a compound represented by the general formula (IV) which ls one of the objective compounds according to the present invention can be prepared by condensing a compound represented by the general formula (II) with a compound represented by the formula (III) in the presence of a base.

Preferable examples of the base to be used in the above condensation include alkali metal hydrides such as sodium hydride and potassium hydride; and alkali metal alcoholares such as sodium methoxide, sodium ethoxide and potassium t-butoxide.

The solvent to be used in the condensation is preferably N,N-dimethylformamide, N,N-dimethylacetamide, N-methylpyrrolidone, tetrahydrofuran or 1,2-dimethoxyethane, though it is not particularly limited.

The reaction temperature is preferably 0 to 100° C., still preferably 20 to 80° C.

Preparation Process 2

A compound represented by the general formula (I) wherein at least one of $R^3$, $R^4$, $R^5$, $R^6$ and $R^7$ is a hydrogen atom or a lower alkyl group can be prepared by the following process:

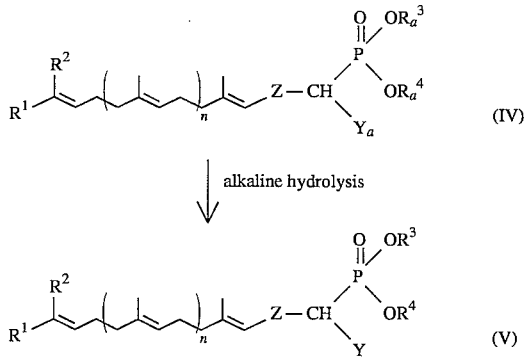

wherein $R^1$, $R^2$, $R^3_a$, $R^4_a$, $Y_a$ Z, n, $R^3$, $R^4$ and Y are each as defined above, with the proviso that at least one of $R^3$, $R^4$, $R^5$, $R^6$ and $R^7$ is a hydrogen atom or a lower alkyl group.

Specifically, a compound represented by the general formula (V) which is one of the objective compounds according to the present invention can be prepared by hydrolyzing the phosphonate ester derivative (IV) prepared in the Preparation process 1 with an alkali such as sodium hydroxide or potassium hydroxide.

The solvent for the reaction is preferably an alcohol such as methanol, ethanol and isopropanol.

The reaction temperature may range from room temperature to the refluxing temperature of the solvent.

Preparation Process 3

When $R^3$, $R^4$, $R^5$, $R^6$ and $R^7$ are each an alkali metal or a lower alkyl group, it can also be prepared by the following process:

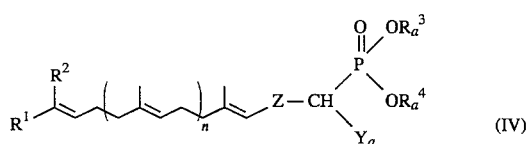

(IV)

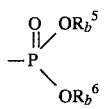

2,4,6-collidine | TMS—Br or
TMS—I

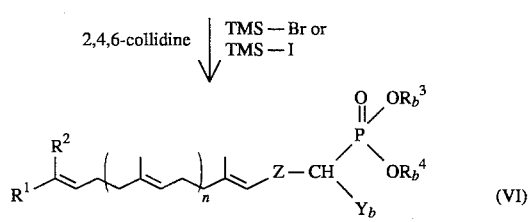

(VI)

wherein $R^3{}_a$, $R^4{}_a$, $Y_a$, Z, n $R^1$ and $R^2$ are each as defined above;

$Y_b$ represents a group represented by the formula:

$$-P\begin{matrix}O & OR_b^5 \\ & \\ & OR_b^6\end{matrix}$$

(wherein $R^5{}_b$ and $R^6{}_b$ may be the same or different from each other and each represent an alkali metal or a lower alkyl group) or a group represented by the formula $-CO_2R^7{}_b$ (wherein $R^7{}_b$ represents an alkali metal or a lower alkyl group); and $R^3{}_b$ and $R^4{}_b$ may be the same or different from each other and each represent an alkali metal or a lower alkyl group.

Specifically, a compound represented by the general formula (VI) which is one of the objective substances according to the present invention can be prepared by reacting the phosphonate ester derivative (IV) prepared in the Preparation process 1 with trimethylsilyl bromide (TMS-Br) or trimethylsilyl iodide (TMS-I) in the presence of 2,4,6-collidine to conduct dealkylation.

The solvent to be used in the above reaction may be any one inert to the reaction, though an example thereof is dichloromethane.

The reaction temperature is preferably 0° to 50° C., still preferably 0° to 30° C.

Preparation Process 4

A compound represented by the general formula (I) wherein $R^3$, $R^4$, $R^5$, $R^6$ and $R^7$ are each an alkali metal or a hydrogen atom can also be prepared by the following process:

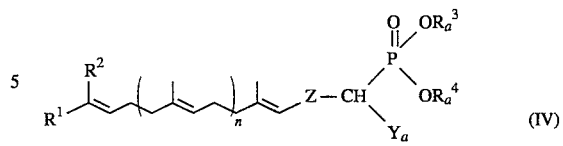

(IV)

1) alkaline hydrolysis
2) TMB—Br or TMS—I/2,4,6-collidine

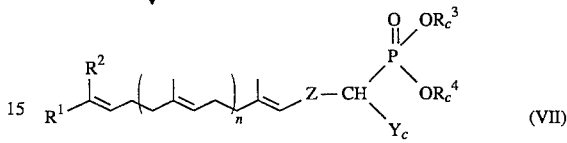

(VII)

wherein $R^3{}_a$, $R^4{}_a$, $Y_a$, Z, n, $R^1$ and $R^2$ are each as defined above;

$Y_c$ represents a group represented by the formula:

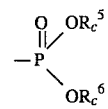

(wherein $R^5{}_c$ and $R^6{}_c$ may be the same or different from each other and each represent an alkali metal or a hydrogen atom) or a group represented by the formula: $-CO_2R^7{}_c$ (wherein $R^7{}_c$ represents an alkali metal or a hydrogen atom); and $R^3{}_c$ and $R^4{}_c$ may be the same or different from each other and each represent an alkali metal or a hydrogen atom.

Specifically, a compound represented by the general formula (VII) which is one of the objective compounds according to the present invention can be prepared by hydrolyzing the phosphonate ester derivative (IV) prepared by the Preparative process 1 with an alkali such as sodium hydroxide or potassium hydroxide and reacting the obtained compound with TMS-Br or TMS-I in the presence of 2,4,6-collidine.

Preparation Process 5

A compound represented by the general formula (I) wherein Z is a group represented by the formula:

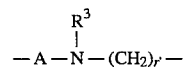

(wherein $R^8$ and A are each as defined above and r' is an integer of 2 to 5); $R^3$ and $R^4$ may the same or different from each other and each represent a hydrogen atom or a lower alkyl group; and Y represents a group represented by the formula:

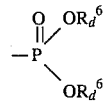

(wherein $R^5{}_d$ and $R_{6d}$ may be the same or different from each other and each represent a hydrogen atom or a lower alkyl group) or a group represented by the formula: $-CO_2R^7{}_d$ (wherein $R^7{}_d$ represents a hydrogen atom or a lower alkyl group) can also be prepared by the following process:

$$R^1 \underset{R^2}{\diagup}\!\!\!\!\!\diagdown \!\!\left(\diagup\!\!\!\diagdown\right)_n \!\!\diagup\!\!\!\overset{R^8}{\diagdown}\!\!A-NH \quad (VIII)$$

+

$$CH_3-\!\!\left\langle\!\!\!\bigcirc\!\!\!\right\rangle\!\!-\!\!\overset{O}{\underset{O}{\overset{\|}{S}}}\!\!-O-(CH_2)_{r'}-CH\!\overset{OR_d^3}{\underset{Y_d}{\diagdown P\diagdown OR_d^4}} \quad (IX)$$

↓ base $$R^1\!\!\diagup\!\!\!\!\diagdown\!\!\overset{R^2}{\left(\diagup\!\!\!\diagdown\right)_n}\!\!\diagup\!\!\!\overset{R^8}{\diagdown}\!\!A-\underset{|}{N}-(CH_2)_{R'}-CH\!\overset{OR_d^3}{\underset{Y_d}{\diagdown P\diagdown OR_d^4}} \quad (X)$$

wherein $R^1$, $R^2$, $R^8$, A, n and r' are each as defined above; $R^3{}_d$ and $R^4{}_d$ may be the same or different from each other and each represent a hydrogen atom or a lower alkyl group; and $Y_d$ represents a group represented by the formula:

$$-\overset{O}{\underset{\diagdown OR_d^6}{\overset{\|}{P}\diagup OR_d^5}}$$

(wherein $R^5{}_d$ and $R^6{}_d$ are each as defined above) or a group represented by the formula: —$CO_2R^7d$ (wherein $R^7{}_d$ is as defined above).

Specifically, a compound represented by the general formula (X) can be prepared by reacting an amine represented by the general formula (VIII) with a tosylate represented by the general formula (IX) in the presence of a base.

The base to be used in the above reaction is preferably potassium carbonate, though it may be any of inorganic and organic ones.

The solvent to be used therein is preferably dimethylformamide or tetrahydrofuran, though it is not particularly limited but may be any one inert to the reaction.

The reaction temperature may range from room temperature to about 60° C.

A representative process for preparing the raw material will now be described.

Preparation Process A

The compound (IX) used in the Preparation process 5 can be prepared by the following process:

$$HO-(CH_2)_{r'}-CH\!\overset{OR_d^3}{\underset{Y_d}{\diagdown P\diagdown OR_d^4}} \quad (XI)$$

↓ $CH_3\!\!-\!\!\left\langle\!\!\!\bigcirc\!\!\!\right\rangle\!\!-\!\!SO_2Cl$

-continued $$CH_3-\!\!\left\langle\!\!\!\bigcirc\!\!\!\right\rangle\!\!-\!\!\overset{O}{\underset{O}{\overset{\|}{S}}}\!\!-O-(CH_2)_{r'}-CH\!\overset{OR_d^3}{\underset{Y_d}{\diagdown P\diagdown OR_d^4}} \quad (IX)$$

wherein r', $R^3{}_d$, $R^4{}_d$ and $Y_d$ are each as defined above.

That is, a compound represented by the general formula (IX) can be prepared by condensing a compound represented by the general formula (XI) with p-toluenesulfonyl chloride in the conventional manner.

The solvent to be used in the above condensation is preferable pyridine or pyridine/tetrahydrofuran, though it may be any one inert to the reaction. When some solvent is used, good results can be attained by conducting the condensation in the presence of a base such as triethylamine to thereby remove formed hydrochloric acid. The reaction temperature is preferably −50° C. to 10° C., still preferably −30° C. to 0° C.

EFFECT OF THE INVENTION

An experimental example will now be given to illustrate the effect of the compound according to the present invention.

Experimental Example

Determination of inhibitory activity against squalene synthetase with liver microsome of cholestyramine-treated rat <Experimental method>

(1) Conditions of Assay 50 mM Tris HCl (pH: 7.4)

1 mM $MgCl_2$ 2 mM KF 1 mM NADPH (nicotinamide adenine dinucleotide phosphate)

10 μM $^3$H-FPP (farnesylpyrophosphoric acid) (10 mCi/mmol, a product of New England Nuclea Co.)

0.1 mg/ml liver microsome of rat 37° C., 10 min.

These components were put in a spit tube as follows:

| | |
|---|---|
| 500 mM Tris HCl (pH: 7.4) | 50 μl |
| 10 mM $MgCl_2$ | 50 μl |
| 2 mM KF | 50 μl |
| 10 mM NADPH | 50 μl |
| sample solution of 5-fold concentration | 100 μl |
| distilled water | 100 μl |
| 1 mg/ml liver microsome of rat | 50 μl |
| | 450 μl |

The obtained mixture was preincubated at 37° C. for 5 minutes. 50 μl of 100 μM $^3$H-FPP (10 mCi/mmol; NEN) was added to the resulting mixture to initiate a reaction. After 10 minutes, 1 ml of 4N NaOH was added to the mixture to stop the reaction, followed by the addition thereto of 1 ml of ethanol. The obtained mixture was incubated at 80° C. for 12 hours, cooled with ice and extracted with petroleum ether twice. The petroleum ether layers were separated from the aqueous layer and evaporated to dryness with nitrogen gas. The residue was dissolved in 25 μl of chloroform containing squalene, farnesol and cholesterol as markers. The obtained solution was applied to TLC (Empore; 412001-1) and developed under the following conditions:

benzene/isopropyl ether (1: 1), 6 min.

heptane, 15 min

The band of squalene was cut from the plate and examined for radioactivity with a liquid scintillation counter to determine the inhibitory ratio.

(2) Preparation of Liver Microsome of Rat

A Sprague-Dawley rat was fed with food containing 2% of cholestyramine (Dowex 1-X2) for at least 5 days to enhance the cholesterol-biosynthesizing activity of the rat. At midnight (0:00), the liver was extirpated from the rat and washed with a 1.154 (w/v) ice-cooled KCl solution to remove the blood from the liver. The resulting liver was cut into small pieces with scissors, homogenized with a Teflon homogenizer of the loose fitting type and subjected to centrifugation (700 g, 10 min). The obtained supernatant was further subjected to centrifugation (15,000 g, 20 min) and the obtained supernatant was furthermore subjected to centrifugation (105,000 g 60 min) to be separated into a microsome fraction and a supernatant. This microsome fraction was washed with a 0.1M potassium phosphate buffer (pH: 7.4) once and suspended in a 0.1 M potassium phosphate buffer in the liver concentration of 3 g/ml. The obtained suspension was examined for protein concentration by the Lowry method and the protein concentration was adjusted to 20 mg/ml.

<Experimental results>

IC50 values of the squalene synthetase inhibiting activity are given in Tables 1 to 5, wherein Me represents a methyl group and Et an ethyl group.

TABLE 1

| Ex. No. | Structure | Inhibitory activity against squalene synthetase ($IC_{50}$, μM) |
|---|---|---|
| 13 | farnesyl-CH(P(ONa)$_2$=O)(P(ONa)$_2$=O) | 0.003 |
| 14 | farnesyl-CH$_2$-CH(P(ONa)$_2$=O)(P(ONa)$_2$=O) | 0.005 |
| 15 | geranyl-CH(P(ONa)$_2$=O)(P(ONa)$_2$=O) | 0.3 |
| 16 | geranylgeranyl-CH(P(ONa)$_2$=O)(P(ONa)$_2$=O) | 0.008 |
| 17 | farnesyl-N(Me)-(CH$_2$)$_3$-CH(P(ONa)$_2$=O)(P(ONa)$_2$=O) | 0.002 |

TABLE 2
| Ex. No. | Structure | Inhibitory activity against squalene synthetase (IC$_{50}$, μM) |
|---|---|---|
| 18 | 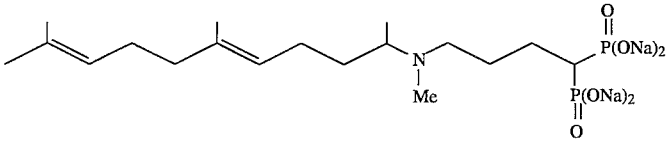 | 0.003 |
| 19 | 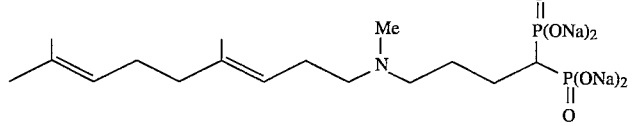 | 0.001 |
| 20 | 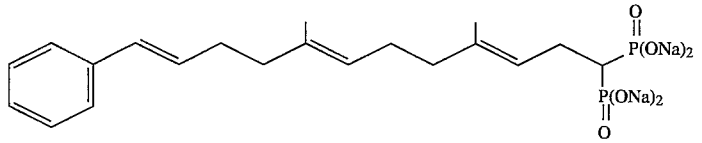 | 0.002 |
| 21 | 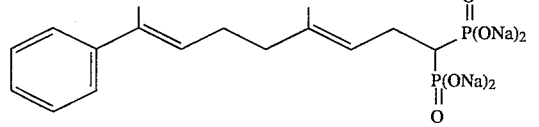 | 0.001 |
| 22 | 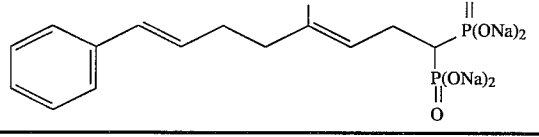 | 0.001 |

TABLE 3

| Ex. No. | Structure | Inhibitory activity against squalene synthetase (IC$_{50}$, μM) |
|---|---|---|
| 23 | Ph-CH=CH-CH$_2$-CH=C(CH$_3$)-CH$_2$-N(Me)-(CH$_2$)$_3$-CH(P(O)(ONa)$_2$)-P(O)(ONa)$_2$ | 0.0005 |
| 29 | farnesyl-CH$_2$-CH(P(O)(OEt)(ONa))(CO$_2$Na) | 7.3 |
| 30 | geranylgeranyl-CH(P(O)(OEt)(ONa))(CO$_2$Na) | 7.1 |
| 31 | farnesyl-CH(P(O)(ONa)$_2$)(CO$_2$Et) | 9.4 |
| 32 | farnesyl-CH(P(O)(ONa)$_2$)(CO$_2$Na) | 1.6 |

TABLE 4

| Ex. No. | Structure | Inhibitory activity against squalene synthetase (IC$_{50}$, μM) |
|---|---|---|
| 33 | farnesyl-(CH$_2$)$_2$-CH(P(O)(ONa)$_2$)(CO$_2$Na) | 0.18 |
| 34 | geranylgeranyl-CH(P(O)(ONa)$_2$)(CO$_2$Na) | 0.6 |
| 35 | farnesyl-N(Me)-(CH$_2$)$_3$-CH(P(O)(ONa)$_2$)(CO$_2$Na) | 0.02 |
| 43 | geranyl-N(Me)-(CH$_2$)$_3$-CH(P(O)(ONa)$_2$)-P(O)(ONa)$_2$ | 0.003 |

TABLE 4-continued

| Ex. No. | Structure | Inhibitory activity against squalene synthetase (IC$_{50}$, μM) |
|---|---|---|
| 44 | (geranyl-N(Et)-CH$_2$CH$_2$CH$_2$-CH(P(ONa)$_2$=O)$_2$) | 0.003 |
| 45 | (geranyl-NH-CH$_2$CH$_2$CH$_2$-CH(P(ONa)$_2$=O)$_2$) | 0.003 |

TABLE 5

| Ex. No. | Structure | Inhibitory activity against squalene synthetase (IC$_{50}$, μM) |
|---|---|---|
| 46 | (farnesyl-N(Me)-(CH$_2$)$_4$-CH(P(ONa)$_2$=O)$_2$) | 0.002 |
| 47 | (geranylgeranyl-NH-CH(P(ONa)$_2$=O)$_2$) | 0.002 |
| 48 | (geranylgeranyl-N(Me)-CH(P(ONa)$_2$=O)$_2$) | 0.001 |
| 49 | (geranylgeranyl-N(Me)-(CH$_2$)$_4$-CH(P(ONa)$_2$=O)$_2$) | 0.002 |
| 51 | (farnesyl-N(Me)-CH$_2$CH$_2$CH$_2$-C(CO$_2$Na)(P(ONa)$_2$=O)) | 0.014 |

It can be understood from the results that the compound of the present invention has an inhibitory activity against squalene synthetase.

Accordingly, the compounds of the present invention are useful as preventive and therapeutic agents for diseases for which a squalene synthetase inhibiting action is efficacious. Although the compounds of the present invention are effective in the prevention and treatment of all diseases for which a squalene synthetase inhibiting action is efficacious, they are efficacious representatively against hyperlipemia. Further, recent studies have revealed that the compounds are also efficacious against solid cancers.

The present invention provides a drug composition comprising a pharmacologically effective amount of a phosphorus-containing isoprenoid derivative represented by the above general formula (I) or a pharmacologically acceptable salt thereof, and a pharmacologically acceptable carrier.

Further, the present invention provides a method of preventing and treating a disease for which a squalene synthetase inhibiting action is efficacious with a phosphorus-containing isoprenoid derivative represented by the general formula (I) or a pharmacologically acceptable salt thereof, and a method of treating hyperlipemia with a phosphorus-containing isoprenoid derivative represented by the general formula (I) or a pharmacologically acceptable salt thereof.

Further, the compounds of the present invention are less toxic and highly safe, thus being valuable also in this sense.

When the compound of the present invention is administered for the treatment and prevention of various diseases as a squalene synthetase inhibitor, it may be orally administered in the form of powder, granule, capsule or syrup or may be parenterally administered as suppository, injection, external preparation or drop. The dose per adult a day is generally about 0.1 to 1,000 mg, which is administered at once or in several portions, though the dose remarkably varies depending upon the symptom, age and the kind of liver trouble.

The pharmaceutical preparation according to the present invention is prepared by using the conventional carrier according to the conventional process.

Specifically, a solid preparation for oral administration according to the present invention is prepared by adding a filler and, if necessary, a binder, a disintegrator, a lubricant, a coloring agent and/or a corrective to a principal agent and shaping the obtained mixture into a tablet, coated tablet, granule, powder or capsule.

The filler includes lactose, corn starch, sucrose, glucose, sorbitol, crystalline cellulose and silicon dioxide; the binder includes polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; the lubricant includes magnesium stearate, talc, polyethylene glycol, silica and hardened vegetable oils; the coloring agent includes those permitted to be added to drugs; and the corrective includes powdered cocoa, menthol, aromatic powder, mentha oil, borneol and powdered cinnamon bark. The tablet and granule according to the present invention may be, of course, coated with sugar, gelatin or the like at need.

An injection according to the present invention is prepared by adding a pH modifier, a buffer, a stabilizer and/or a solubilizing agent to a principal agent at need and formulating the obtained mixture into a subcutaneous, intramuscular or intravenous injection according to the conventional process.

EXAMPLE

Examples of the present invention will now be described, though it is needless to say that the present invention is not limited to them. In the Examples, Me represents a methyl group and Et an ethyl group.

The preparation of the raw materials for preparing the compounds of the present invention will be described in the following Preparative Examples precedent to the Examples.

PREPARATIVE EXAMPLE 1

(E,E)-N.N-Diformyl-3,7,11-trimethyl-2,6,10-dodecatrienylamine

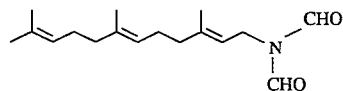

30 g of farnesyl bromide was dissolved in 30 ml of dimethylformamide. The obtained solution was stirred at room temperature, followed by the addition thereto of 12 g of sodium N,N-diformylamide. The obtained mixture was heated to 50° C. and stirred for 3 hours.

The resulting mixture was poured into 1N hydrochloric acid. The obtained mixture was extracted with ethyl acetate thrice. The ethyl acetate layers were together washed with water and a saturated aqueous solution of common salt successively, dried over anhydrous magnesium sulfate, and distilled in a vacuum to remove the solvent, giving a crude oil.

This crude oil was purified by silica gel column chromatography (solvent: ethyl acetate/n-hexane) to give 27.3 g of the title compound.

$^1$H-NMR(CDCl$_3$); δ(ppm) 1.57(6H, s), 1.59(3H, s), 1.65(3H, s), 1.78(3H, s), 1.94–2.10(8H, m), 4.23(2H, d, J=7Hz), 5.03–5.10(2H, m), 5.10–5.17(1H, m), 8.93(2H, s)

PREPARATIVE EXAMPLE 2

(E,E)-N-Formyl-3,7,11-trimethyl-2,6,10-dodecatrienylamine

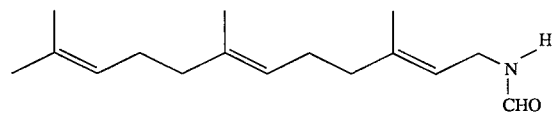

27.3 g of the compound prepared in the Preparative Example 1 was dissolved in 300 ml of ethanol, followed by the addition thereto of 120 cc of 1N sodium hydroxide. The obtained mixture was stirred at room temperature for one hour, followed by the addition thereto of ice-water. The resulting mixture was extracted with ethyl acetate twice. The ethyl acetate layers were together washed with a saturated aqueous solution of common salt, dried over anhydrous magnesium sulfate and distilled in a vacuum to remove the solvent and 20.7 g of the title compounds was obtained.

$^1$H-NMR(CDC13); δ(ppm) 1.60(6H, s), 1.65(6H, s), 1.95–2.15(8H, m), 3.90–3.95(2H, m), 5.05–5.10(2H, m), 5.15–6.03(1H, m), 8.15(1H, bs)

PREPARATIV EXAMPLE 3

(E,E)-N-Methyl-3,7,11-trimethyl-2,6,10-dodecatrienlyamine

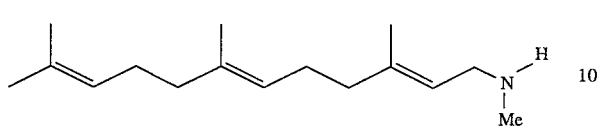

15.7 g of the compound prepared in the Preparative Example 2 was dissolved in 450 ml of tetrahydrofuran, followed by the addition thereto of 4.8 g of aluminum lithium hydride in portions. The obtained mixture was stirred at room temperature for 30 minutes, refluxed for 2 hours and brought to room temperature. 450 ml of tetrahydrofuran was added to the resulting mixture, followed by the addition thereto of 5 ml of water, 5 ml of 15% aqueous sodium hydroxide and 15 ml of water in this order. The obtained mixture was filtered through Celite to remove the formed precipitate, which was washed with tetrahydrofuran. The filtrate was distilled in a vacuum to remove the solvent. 14.6 g of the title compound was obtained.

$^1$H-NMR(CDCl$_3$); δ(ppm) 1.60(6H, s), 1.63(3H, s), 1.68(3H, s), 1.95–2.15(8H, m), 2.40(3H, s), 3.18(2H, d, J=7Hz), 5.05–5.15(2H, m), 5.22–5.30(1H, m)

PREPARATIVE EXAMPLE 4

(E,E)-N-(3-Chloropropyl)-N-methyl-3,7,11-trimethyl-2,6,10-dodecatrienylamine

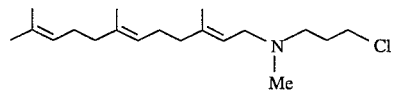

9.0 g of the compound prepared in the Preparative Example 3 was dissolved in 20 ml of dimethylformamide, followed by the addition thereto of 4.7 ml of 1-bromo-3-chloropropane and 6.7 ml of triethylamine. The obtained mixture was stirred overnight.

The resulting mixture was poured into ice-water and the obtained mixture was extracted with ethyl acetate thrice. The ethyl acetate layers were together washed with water and a saturated aqueous solution of common salt successively, dried over anhydrous magnesium sulfate, and distilled in a vacuum to remove the solvent. A crude oil was obtained.

This crude oil was purified by silica gel column chromatography (solvent: dichloromethane/methanol) to give 11.2 g of the title compound.

$^1$H-NMR(CDCl$_3$); δ(ppm) 1.60(6H, s), 1.63(3H, s), 1.70(3H, s), 1.95–2.00(4H, m), 2.00–2.15(6H, m), 2.20(3H, s), 2.45(2H, t, J=6Hz), 2.98(2H, d, J=10Hz), 3.60(2H, t, J=7Hz), 5.05–5.15(2H, m), 5.22–5.28(1H, m)

PREPARATIVE EXAMPLES 5 AND 6

The following compounds were prepared in a similar manner to that of the Preparative Examples 1 to 4.

PREPARATIVE EXAMPLE 5

(E)-N-(3-Chloropropyl)-N-methyl-4,8-dimethyl-3,7-nonadienylamine

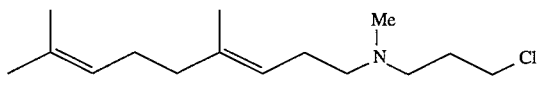

$^1$H-NMR(CDCl$_3$): δ(ppm) 1.60(3H,s), 1.62(3H, s), 1.68(3H, s), 1.96–2.13(6H, m), 2.20–2.30(2H, m), 2.35(3H, s), 2.41–2.54 ( 2H, m), 2.55–2.66 (2H, m), 3.62(2H, t, J=6Hz), 5.05–5.14(2H, m)

PREPARATIVE EXAMPLE 6

(E)-N-(3-Chloropropyl)-N-methyl-1,5,9-trimethyl-4,8-decadienylamine

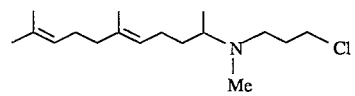

$^1$H-NMR(CDCl$_3$); δ(ppm) 0.93(3H, s), 1.17–1.30(2H, m), 1.60(6H, s), 1.67(3H, s), 1.90–1.95(2H, m), 1.96–2.13(6H, m), 2.18(3H, s), 2.43–2.65(3H, m), 3.61(2H, t, J=7Hz), 5.06–5.16(2H, m)

PREPARATIVE EXAMPLE 7

4-TetrahydropyranyloxybutYl-1,1-bis(phosphonic acid diethyl)

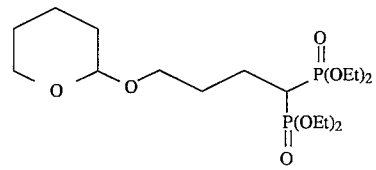

1.5 g of sodium hydride (55% oil suspension) was suspended in 50 ml of anhydrous tetrahydrofuran, followed by the dropwise addition thereto of 10 g of tetraethyl methylenedlphosphonate under stirring at room temperature. The obtained mixture was stirred for 30 minutes, followed by the addition thereto of 8.5 g of 3-bromo-1-tetrahydropyranyloxypropane. The obtained mixture was stirred at 60° C. overnight. 250 ml of ice-water was added to the resulting mixture, followed by extraction with 100 ml of n-hexane. The aqueous layer was extracted with 200 ml of dichloromethane. The organic layer was washed with a saturated aqueous solution of common salt, dried over anhydrous magnesium and concentrated to give 8.4 g of the title compound as a colorless oil.

$^1$H-NMR(CDCl$_3$); δ(ppm) 1.33(12H, t, J=8Hz), 1.45–1.60(4H, m), 1.65–1.90(4H, m), 1.90–2.10(2H, m), 2.35(1H, tt, J=6.4Hz, 24Hz), 3.36–3.42(1H, m), 3.46–3.53(1H, m), 3.71–3.77(1H, m), 3.82–3.88(1H, m), 4.12–4.22(8H, m), 4.56–4.58(1H, m)

PREPARATIVE EXAMPLE 8

4-Hydroxybutyl-1,1-bis(phosphonic acid diethyl)

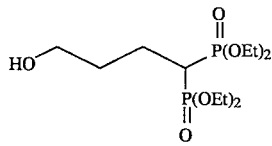

8.4 g of the 4-tetrahydropyranyloxybutyl-1,1-bis(phosphonic acid diethyl) prepared in the Preparative Example 7 was dissolved in 50 ml of methanol, followed by the addition thereto of 2g of Dowex 50W X8 ($H^+$ type, 100- to 200-mesh). The obtained mixture was refluxed for 2 hours, cooled and filtered to remove the resin. The filtrate was concentrated to give 6.7 g of the title compound as a colorless oil.

$^1$H-NMR(CDCl$_3$); δ(ppm) 1.33(12H, t, J=8Hz), 1.78–1.84(2H, m), 1.92–2.13(2H, m), 2.36(1H, tt, J=6.4Hz, 24Hz), 3.65(2H, t, J=6Hz), 4.12–4.21(8H, m)

PREPARATIVE EXAMPLE 9

4-p-Tolylsulfonyloxybutyl-1,1-bis(phosphonic acid diethyl)

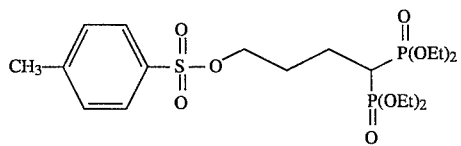

8.8 g of the 4-hydroxybutyl-1,1-bis(phosphonic acid diethyl) prepared in the Preparative Example 8 was dissolved in 20 ml of pyridine. 7.2 g of p-toluene-sulfonyl chloride was added to the obtained solution in portions under cooling with ice and stirring. The obtained mixture was stirred under cooling with ice for 5 hours, followed by the addition thereto of 500 ml of ice-water. The obtained mixture was stirred as such for 30 minutes and extracted with 200 ml of ethyl acetate twice. The ethyl acetate layers were together washed with dilute hydrochloric acid, an aqueous solution of sodium hydrogencarbonate and a saturated aqueous solution of common salt successively, dried over anhydrous magnesium sulfate, and distilled to remove the solvent. The residue was purified by silica gel column chromatography [Merk, 230- to 400-mesh, eluent: dichloromethane/acetone (1 : 1)] to give 7.0 g of the title compound as a colorless oil.

$^1$H-NMR(CDCl$_3$); δ(ppm) 1.31(12H, t, J=8Hz), 1.86–2.04(4H, m), 2.23(1H, tt, J=6.4Hz, 24Hz), 2.44(3H, s), 4.02(2H, t, J=5Hz), 4.08–4.22(8H, m), 7.33(2H, d, J=8.4Hz), 7.77(2H, d, J=8.4Hz)

EXAMPLE 1

(E,E)-4,8,12-Trimethyl-3,7,11-tridecatrienyl-1,1-bis(phosphonic acid diethyl)

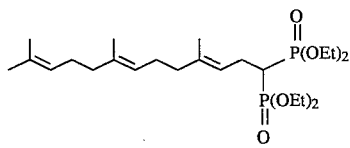

0.436 g of 55% sodium hydride was suspended in 10 ml of dimethylformamide, followed by the dropwise addition thereto of a solution of 2.88 g of tetraethyl methylenediphosphonate in 5 ml of dimethylformamide under cooling with ice. Then, a solution of 2.85 g of farnesyl bromide in 5 ml of dimethylformamide was added to the obtained mixture. The obtained mixture was stirred at room temperature overnight and poured onto ice-water. The resulting mixture was acidified with dilute hydrochloric acid and extracted with ethyl acetate twice. The ethyl acetate layers were together washed with water, dried over magnesium sulfate, and distilled in a vacuum to remove the solvent, giving a crude oil.

This crude oil was purified by silica gel column chromatography (solvent: chloroform/methanol) to give 1.0 g of the title compound as a colorless oil.

$^1$H-NMR(CDCl$_3$); δ(ppm) 1.35(12H, dt, J=1.2, 7.0Hz), 1.59(3H, s), 1.60(3H, s), 1.64(3H, s), 1.68(3H, s), 1.93–2.12(8H, m), 2.22–2.40(1H, m), 2.58–2.72(2H, m), 4.06–4.22(8H, m), 5.04–5.18(2H, m), 5.28–5.37(1H, m)

EXAMPLES 2 TO 11

The following compounds were prepared in a similar manner to that of the Example 1.

EXAMPLE 2

(E,E)-5,9,13-Trimethyl-4,8,12-tetradecatrienyl-1,1-bis(phosphonic acid diethyl)

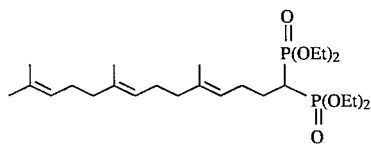

¹H-NMR (CDCl₃ ); δ(ppm) 1.36(12H, t, J=7.0Hz), 1.60(3H, s), 1.62(3H, s), 1.67(3H, s), 1.88–2.14 ( 10H, m), 2.21–2.40 ( 3H, m), 4.11–4.22(8H, m), 5.06–5.17 (3H, m)

EXAMPLE 3

(E)-4,8-Dimethyl-3,7-nonadienyl-1,1-bis(phosphonic acid diethyl)

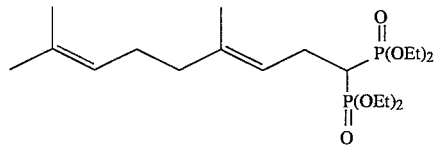

¹H-NMR(CDCl₃); δ(ppm) 1.37(12H, t, J=7.0Hz), 1.59(3H, s), 1.62(3H, s), 1.64(3H, s), 1.96–2.10 (4H, m), 2.23–2.39 (1H, m), 2.57–2.70 (2H, m), 4.12–4.22(8H, m), 5.06–5.13 (1H, m), 5.28–5.34 (1H, m)

EXAMPLE 4

(E,E,E)-4,8,12,16-Tetramethyl-3,7,11,15-heptadeca-tetraenyl-1,1-bis(phosphonic acid diethyl)

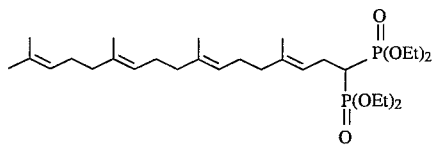

¹H-NMR(CDCl₃); δ(ppm) 1.33(12H, t, J=7.0 Hz), 1.60(9H, s), 1.64(3H, s), 1.67(3H, s), 1.95–2.12(12H, m), 2.23–2.38(1H, m), 2.57–2.70(2H, m), 4.12–4.21 (8H, m), 5.06–5.14(3H, m), 5.28–5.34(1H, m)

EXAMPLE 5

4-{(E,E)-N-Methyl-3,7,11-trimethyl-2,6,10-dodeca-trienylamino}butyl-1,1-bis(phosphonic acid diethyl)

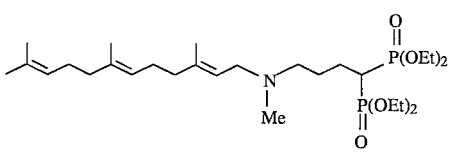

¹H-NMR(CDCl₃); δ(ppm) 1.35(12H, t, J=6Hz), 1.60(3H, s), 1.65(3H, s), 1.70(6H, s), 1.75–1.80(2H, m), 1.85–2.15(10H, m), 2.15(3H, s), 2.25–2.40(3H, m), 2.95(2H, d, J=7Hz), 4.10–4.20(8H, m), 5.05–5.15(2H, m), 5.20–5.25(1H, m)

EXAMPLE 6

4-{(E)-N-Methyl-1,5,9-trimethyl-4,8-decadienylamino}-butyl-1,1-bis(phosphonic acid diethyl)

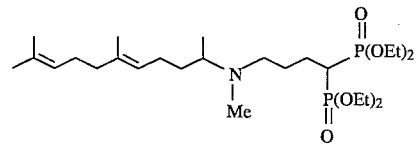

The title compound was prepared from the (E)-N-(3-chloropropyl)-N-methyl-1,5,9-trimethyl-4,8-decadienyl-amine prepared in the Preparative Example 6 in a similar manner to that of Example 1.

¹H-NMR(CDCl₃); δ(ppm) 0.90–0.95(8H, d, J=7Hz), 1.20–1.35(2H, m), 1.35(12H, t, J=6Hz), 1.60(6H, s), 1.68(3H, s), 1.85–2.10(10H, m), 2.15(3H, s), 2.23–2.43(3H, m), 2.58–2.65(1H, m), 4.13–4.22(8H, m), 5.08–5.15(2H, m)

EXAMPLE 7

4-{(E)-N-Methyl-4,8dimethyl-3,7-nonadienylamino}-butyl-1,1-bis(phosphonic acid diethyl)

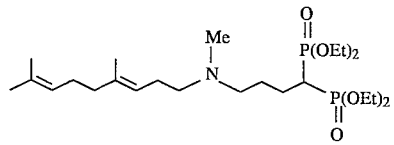

The title compound was prepared from the (E)-N-(3-chloropropyl)-N-methyl-4,8-dimethyl-3,7-nonadienylamine prepared in the Preparative Example 5 in a similar manner to that of Example 1.

¹H-NMR(CDCl₃); δ(ppm) 1.35(12H, t, J=6Hz), 1.60(3H, s), 1.62(3H, s), 1.67(3H. s), 1.70–2.10(8H, m), 2.15–2.50(10H, m). 4.15–4.25(8H, m), 5.05–5.15(2H, m)

EXAMPLE 8

(E,E,E)-4,8-dimethyl-12-phenyl-3,7,11-dodecatrienyl-1,1-bis(phosphonic acid diethyl)

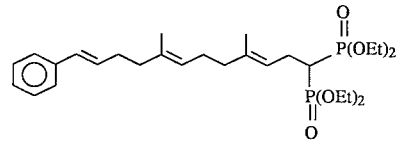

¹H-NMR (CDCl₃); δ(ppm) 1.33(12H, dt, J=6.5, 1.5Hz), 1.62(3H, s), 1.64(3H, s), 1.97–2.20 ( 2H, m), 2.05–2.16 (4H, m), 2.23–2.38(3H, m), 2.57–2.70(2H, m), 4.12–4.20(8H, m), 5.16(1H, t, J=7Hz), 5.41(1H, t, J=7Hz), 6.20(1H, dt, J=18.7Hz), 6.38(1H, d, J=7Hz), 7.16–7.21(1H, m), 7.25–7.35(4H, m)

EXAMPLE 9

(E,E)-4-Methyl-8-phenyl-3,7-nonadienyl-1,1-bis(phosphonic acid diethyl)

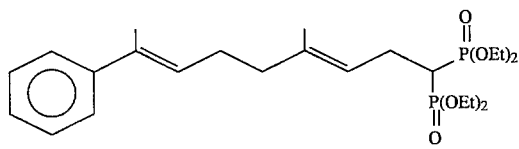

$^1$H-NMR(CDCl$_3$); δ(ppm) 1.29(12H, dt, J=6.5, 1Hz), 1.53(3H, s), 1.97–2.08(4H, m), 2.00(3H, s), 2.27(1H, tt, J=26.5, 6.5Hz), 2.49(2H, tt, J=17, 6.5Hz), 4.08–4.14(8H, m), 5.24(1H, t, J=6.5Hz), 5.42(1H, t, J=6.5Hz), 7.16(2H, br.d, J=6.5Hz), 7.22(1H, t, J=6.5Hz), 7.32(2H, t, J=6.5Hz)

EXAMPLE 10

(E,E)-4-Methyl-8-phenyl3,7-octadienyl-1,1-bis-(phosphonic acid diethyl)

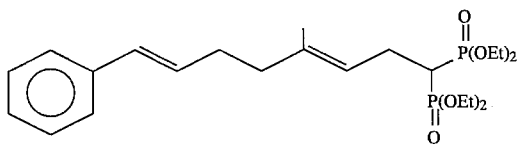

$^1$H-NMR (CDCl$_3$); δ(ppm) 1.32(12H, dt, J=7.5, 1.5Hz), 1.62(3H, s), 2.11–2.17(2H, m), 2.31(1H, tt, J=24, 6.5Hz), 2.40–2.46(2H, m), 2.57–2.70(2H, m), 4.10–4.20(8H, m), 5.33(1H, t, J=6.5Hz), 5.63(1H, dt, J=12, 6.5Hz), 6.40(1H, d, J=12Hz), 7.18–7.34 (5H, m)

EXAMPLE 11

4-{(E,E)-N-Methyl-3-methyl-7-phenyl-2,6-octadienyl-amino}butyl- 1,1-bis(phosphonic acid diethyl)

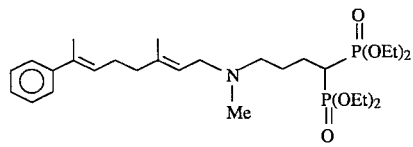

$^1$H-NMR(CDCl$_3$); δ(ppm) 1.43(12H, t, J=7Hz), 1.52(3H, s), 1.70–1.84(2H, m), 1.85–2.00(2H, m), 2.01(3H, s), 2.00–2.11(4H, m), 2.19(3H, br.s), 2.30–2.40(2H, m), 232(1H, tt, J=24, 6.5Hz), 2.91–3.02(2H, m), 5.20(1H, t, J=6.5Hz), 5.42(1H, t, J=7Hz), 7.16(2H, br.d, J=8Hz), 7.22(1H, t, J=7.5Hz), 7.32(2H, t, J=7.5Hz)

EXAMPLE 12

(E,E)-4,8,12-Trimethyl-3,7,11-tridecatrienyl-1,1-bis-(phosphonic acid ethyl sodium salt)

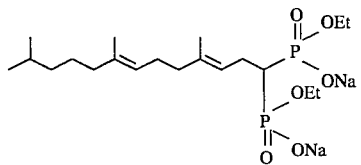

1 g of the (E,E)-4,8,12-trimethyl-3,7,11-tridecatrienyl-1,1-bis(phosphonic acid diethyl) prepared in Example 1 was dissolved in a mixture comprising 5 ml of ethanol and 5 ml of water, followed by the addition thereto of 0.49 g of sodium hydroxide. The obtained mixture was refluxed for 6 hours, cooled, acidified with dilute hydrochloric acid, and extracted with ethyl acetate twice. The ethyl acetate layers were together washed with water, dried over magnesium sulfate and distilled in a vacuum to remove the solvent, giving a crude oil.

This crude oil was purified by silica gel column chromatography (solvent: chloroform/methanol) and dissolved in 10 ml of ethanol, followed by the addition thereto of 88 mg of sodium hydroxide. The obtained mixture was stirred for 30 minutes.

The resulting mixture was distilled in a vacuum to remove the solvent. The residue was dissolved in water. The obtained solution was subjected to CHP—20—P gel column chromatography (solvent: water/acetonitrile) and the eluate was freeze-dried to give 0.14 g of the title compound as a white solid.

MASS(FAB); m/z 503(M+Na)$^+$ $^1$H-NMR(D$_2$O); δ(ppm) 1.08(6H, t, J=7.0Hz), 1.48(6H, s), 1.50(3H, s), 1.54(3H, s), 1.70–2.04(9H, m), 2.28–2.44(2H, m), 3.66–3.82(4H, m), 5.00–5.12(2H, m)

EXAMPLE 13

(E,E)-4,8,12-Trimethyl-37,11-tridecatrienyl-1,1-bis-(phosphonic acid disodium salt)

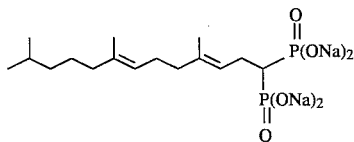

0.8 g of the (E,E)-4,8,12-trimethyl-3,7,11-tridecatrienyl-1,1-bis(phosphonic acid diethyl) prepared in Example 1 was dissolved in 10 ml of dichloromethane, followed by the addition thereto of 0.43 ml of 2,4,6-collidine under cooling with ice. Then, 1.3 ml of bromotrimethylsilane was added to the obtained mixture, and the resulting mixture was stirred at room temperature overnight.

The solvent was distilled off in a vacuum and 5 ml of methanol was added to the residue. The obtained mixture was stirred for 20 minutes and distilled to remove the solvent. The residue was dissolved again in 5 ml of methanol, followed by the addition thereto of 0.27 g of sodium hydroxide. The obtained mixture was stirred for 30 minutes and distilled in a vacuum to remove the solvent. The residue was dissolved in water and the obtained solution was subjected to CHP—20—P gel column chromatography (solvent: water/acetonitrile). The eluate was freeze-dried to give 0.16 g of the title compound.

$^1$H-NMR(D$_2$O); δ(ppm) 1.47(3H, s), 1.49(3H, s), 1.52(3H, s), 1.54(3H, s), 1.58–1.73(1H, m), 1.79–2.08(8H, m), 2.28–2.43(2H, m), 5.00–5.14(2H, m), 5.31–5.39(1H, m)

EXAMPLES 14 TO 23

The following compounds were prepared in a similar manner to that of the Example 13.

EXAMPLE 14

(E,E)-5,9,13-Trimethyl-4,8,12-tetradecatrienyl-1,1-bis(phosphonic acid disodium salt)

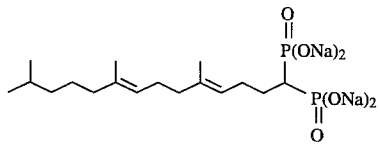

$^1$H-NMR(D$_2$O); δ(ppm) 1.47(6H, s), 1.51(3H, s), 1.54(3H, s), 1.56–1.77(3H, m), 1.84–2.15 (10H, m), 5.01–5.11 (2H, m), 5.13–5.20(1H, m)

EXAMPLE 15

(E)-4,8-Dimethyl3,7-nonadienyl-1,1-bis(phosphonic acid disodium salt)

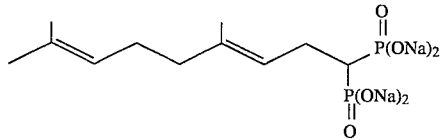

$^1$H-NMR(D$_2$O); δ(ppm) 1.48(6H, s), 1.52(3H, s), 1.54(3H, s), 1.63–1.80(1H, m), 1.87–2.02(4H, m), 2.21–2.42(2H, m), 5.04–5.12 (1H, m), 5.30–5.36(1H, m)

EXAMPLE 16

(E,E,E)-4,8,12,16-Tetramethyl-3,7,11,15-heptadecatetraenyl-1,1-bis(phosphonic acid disodium salt)

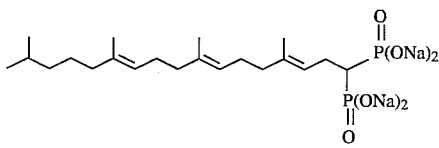

$^1$H-NMR(D$_2$O); δ(ppm) 1.47(6H, s), 1.49(3H, s), 1.52(3H, s), 1.54(3H, s), 1.57–1.70(1H, m), 1.84–2.03 (12H, m), 2.30–2.42(2H, m), 5.00–5.13(3H, m), 5.35–5.40(1H, m)

EXAMPLE 17

4-{(E,E)-N-Methyl-3,7,11-trimethyl-2,6,10-dodecatrienylamino}butyl-1,1-bis(phosphonic acid disodium salt)

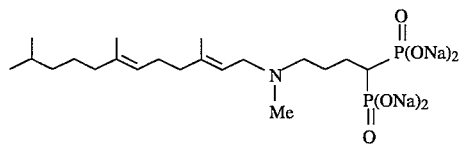

$^1$H-NMR(D$_2$O); δ(ppm) 1.45(6H, s), 1.50(6H, s), 1.55–1.70(5H, m), 1.85–1.90(2H, m), 1.92–2.08(6H, m), 2.15(3H, s), 2.40–2.46(2H, m), 3.05(2H, d, J=9Hz), 5.00–5.05 (2H, m), 5.10–5.17(1H, m)

EXAMPLE 18

4-{(E)-N-Methyl-1,5,9-trimethyl-4,8-decadienylamino}-butyl-1,1-bis(phosphonic acid disodium salt)

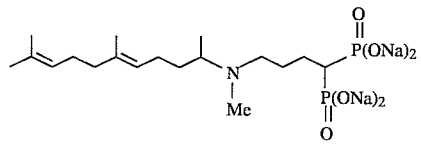

$^1$H-NMR(D$_2$O); δ(ppm) 1.00 (3H, d, J =7Hz ), 1.20–1.33(2H, m), 1.48(6H, s), 1.55(3H, s), 1.55–1.70(4H, m), 1.83–2.00(7H, m), 2.25(3H, s), 2.55–2.63 (2H, m), 2.78–2.87(1H, m), 5.02–5.12 (2H, m)

EXAMPLE 19

4-{(E)-N-Methyl-4,8-dimethyl-3,7-nonadienylamino}-butyl-1,1-bis(phosphonic acid disodium salt)

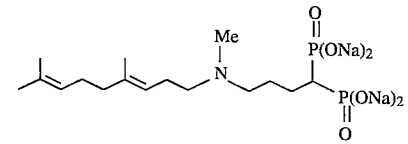

$^1$H-NMR(CDCl$_3$); δ(ppm) 1.45(3H, s), 1.48(3H, s), 1.53(3H, s), 1.55–1.68(5H, m), 1.85–1.92(2H, m), 1.95–2.00(2H, m), 2.05–2.15(2H, m), 2.18(3H, s), 2.33–2.43(4H, m), 5.00–5.08(2H, m)

EXAMPLE 20

(E,E,E)-4,8-Dimethyl-12-phenyl-3,7,11-dodecatrienyl-1,1-bis(phosphonic acid disodium salt)

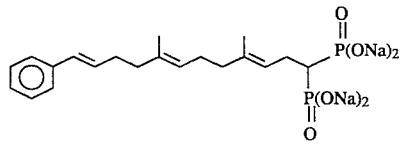

¹H-NMR(D₂O); δ(ppm) 1.50(3H, s), 1.52(3H, s), 1.69(1H, tt, J=21, 7Hz), 1.86–1.90(2H, m), 1.96–2.07(4H, m), 2.18–2.24(2H, m), 2.30–2.42(2H, m), 5.16(1H, t, J=7Hz), 5.34(1H, t, J=7Hz), 6.22(1H, dt, J=16, 7Hz), 6.34(1H, d, J=16Hz), 7.12(1H, t, J=7.5Hz), 7.23(2H, t, J:7.5Hz), 7.30(2H, d, J=7.5Hz)

EXAMPLE 21

(E,E)-4-Methyl-8-phenyl-3,7-nonadienyl-1,1-bis-(phosphonic acid disodium salt)

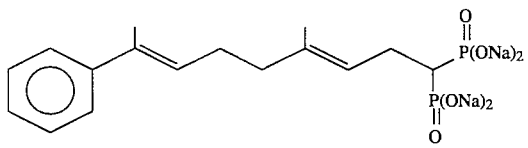

¹H-NMR (D₂O); δ(ppm) 1.40(3H, s), 1.61(1H, tt, J=19, 6.5Hz), 1.86(3H, s), 1.91–1.98(4H, m), 2.27–2.38(2H, m), 5.31(1H, t, J=6.5Hz), 5.45(1H, t, J=6.5Hz), 7.15–7.19(3H, m), 7.28(2H, t, J=6.5Hz)

EXAMPLE 22

(E,E)-4-Methyl-8-phenyl-3,7-octadienyl-1,1-bis-(phosphonic acid disodium salt)

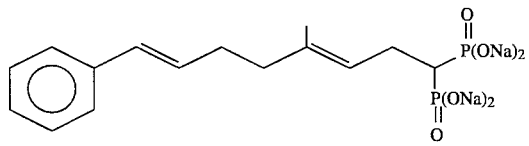

¹H-NMR(D₂O); δ(ppm) 1.48(3H, s), 1.61(1H, tt, J=16, 6HZ), 2.01–2.07(2H, m), 2.30–2.41(4H, m), 5.38–5.43(1H, m), 5.16(1H, dt, J=13, 6Hz) , 6.34(1H, d, J=3Hz), 7.12–7.33(5H, m)

EXAMPLE 23

4-{(E,E)-N-Methyl-3-methyl-7-phenyl-2,6-octadienyl-amino}-butyl- 1,1-bis(phosphonic acid disodium salt)

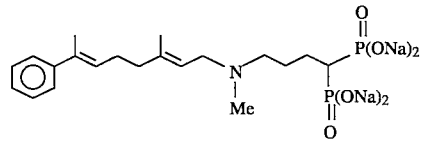

¹H-NMR(D₂O); δ(ppm) 1.39(3H, s), 1.61–1.77(5H, m), 1.87(3H, s), 1.99–2.40(4H, m), 2.36(3H, s), 2.70(2H, t, J=6.5Hz), 3.29(2H, d, J=7Hz), 5.11(1H, t, J=7Hz), 5.39–5.42(1H, m), 7.14(2H, br.d, J=7.5Hz), 7.18(1H, br.t, J=7.5Hz), 7.28(2H, br.t, J=7.5Hz)

EXAMPLE 24

Diethyl (E,E)-1-carboethoxy-4,8,12-trimethyl-3,7,11-tridecatrienylphosphonate

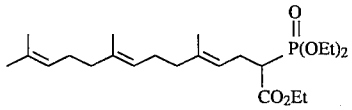

0.59 g of 55% sodium hydride was suspended in 5 ml of N,N-dimethylformamide in a nitrogen atmosphere, followed by the dropwise addition thereto of 5 ml of a solution of 3.0 g of ethyl diethylphosphonoacetate in N,N-dimethylformamide at room temperature. The obtained mixture was stirred for 10 minutes. 5 ml of a solution of 4.5 g of farnesyl bromide in N,N-dimethylformamide was added to the resulting mixture at room temperature. The obtained mixture was further stirred for one hour, followed by the addition thereto of ice-water. The resulting mixture was extracted with ethyl acetate. The organic layer was washed with a saturated aqueous solution of common salt, dried over anhydrous magnesium sulfate and distilled in a vacuum to remove the solvent. The obtained crude product was purified by silica gel column chromatography (solvent: n-hexane/ethyl acetate) to give 2.6 g of the title compound as a colorless oil.

¹H-NHR(CDCl₃); δ(ppm) 1.27(3H, t, J=7.0Hz), 1.34 (6H, dt, J= 2.0, 7.0Hz ), 1.58(3H, s), 1.60(3H, s), 1.63(3H, s), 1.67(3H, s), 1.93–2.12(8H, m), 2.46–2.58(1H, m), 2.89–2.98(1H, m), 4.10–4.22(6H, m), 2.63–2.76(1H, m), 2.89–2.98(1H, m), 4.10–4.22(6H, m), 5.02–5.14(3H, m)

EXAMPLES 25 TO 27

The following compounds were prepared in a similar manner to that of Example 24.

EXAMPLE 25

Diethyl (E,E,-1-carboethoxy-5,9,13-trimethyl-4,8,12-tetradecatrienylphosphonate

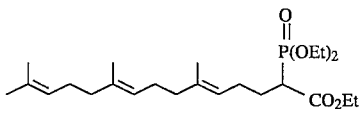

$^1$H-NMR(CDCl$_3$); δ(ppm) 1.28(3H, t, J=7.0Hz), 1.32 (6H, td, J=7.0, 2.0Hz), 1.57(3H, s), 1.59(6H, s), 1.68(3H, s), 1.94–2.10(12H, m), 2.90–3.00(1H, m), 4.08–4.26(6H, m), 5.04–5.12(3H, m)

EXAMPLE 26

Diethyl (E,E,E)-1-carboethoxy-6,10,14-trimethyl-3,5,9,13-pentadecatetraenylphosphonate

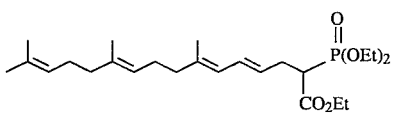

$^1$H-NMR(CDCl$_3$); δ(ppm) 1.26(3H, t, J=7.0Hz), 1.34(6H, td, J=7.0, 2.0Hz), 1.59(6H, s), 1.67(3H, s), 1.72(3H, s), 1.94–2.18 (8H, m), 2.56–2.80(2H, m), 2.94–3.04 (1H, m), 4.10–4.23(6H, m), 5.04–5.16 (2H, m), 5.45(1H, dr, J=15.0, 5.5Hz), 5.76(1H, d, J=10.0Hz). 6.31(1H, dd, J=15.0, 10.0Hz)

EXAMPLE 27

Diethyl, 1-carboethoxy-4-{(E,E)-N-methyl-3,7,11-trimethyl-2,6,10-dodecatrienylamino}butylphosphonate

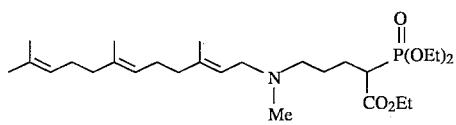

$^1$H-NMR(CDCl$_3$); δ(ppm) 1.25–1.37(9H, m), 1.60(6H, s), 1.62(3H, s), 1.68(3H, s), 1.75–1.90(4H, m), 1.93–2.15(8H, m), 2.18(3H, s), 2.10–2.18(2H, m), 2.90–3.00(3H, m), 4.10–4.23(6H, m), 5.08–5.15(2H, m), 5.20–5.08(1H, m)

EXAMPLE 28

Disodium salt of ethyl (E,E)-1-carboxy-4,8,12-trimethyl-3,7,11-tridecatrienylphosphonate

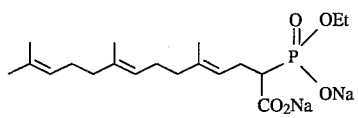

A mixture comprising 0.50 g of the diethyl (E,E)- 1-carboethoxy-4,8,12-trimethyl-3,7,11-tridecatrienylphosphonate prepared in the Example 24, 0.50 g of sodium hydroxide, 10 ml of ethanol and 2 ml of water was heated under reflux for 10 hours, cooled and acidified with 2N hydrochloric acid. The resulting mixture was extracted with ethyl acetate. The organic layer was washed with a saturated aqueous solution of common salt, dried over anhydrous magnesium sulfate and distilled in a vacuum to remove the solvent. 0.32 g of a crude oil was obtained.

0.05 g of this crude oil was purified by dissolving it in 1 ml of 1N aqueous sodium hydroxide and subjecting the obtained solution to CHP—20—P gel column chromatography (solvent: water/acetonitrile). 0.02 g of the title compound was obtained as a white solid.

$^1$H-NMR(D$_2$O); δ(ppm) 1.09(3H, dt, J=2.0, 7.0Hz), 1.47(6H, s), 1.49(3H, s) 1.49(3H, s), 1.54(3H, s), 1.84–2.01(8H, m), 2.16–2.40(2H, m), 2.40–2.53(1H, m), 3.73–3.84(2H, m), 4.98–5.10(3H, m)

EXAMPLES 29 AND 30

The following compounds were prepared in a similar manner to that of Example 28.

EXAMPLE 29

Disodium salt of ethyl(E,E)-1-carboxy-5,9,13-trimethyl-4,8,12-tetradecatrienylphosphonate

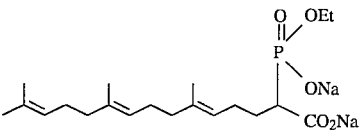

$^1$H-NMR(D$_2$O); δ(ppm) 1.08(3H, t, J=7.0Hz), 1.47(9H, s), 1.55(3H, s) 1.70–2.02(12H, m), 2.44–2.55(1H, m), 3.72–3.82(2H, m), 5.01–5.12(3H, m)

EXAMPLE 30

Disodium salt of ethyl (E,E,E)-1-carboxy-6,10,14-trimethyl-3,5,9,13-pentadecatetraenylphosphonate

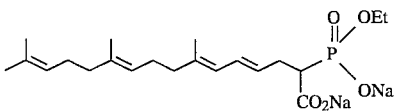

¹H-NMR(D₂O); δ(ppm) 1.08(3H, t, J=7.0Hz), 1.46(6H, s), 1.53(3H, s) 1.59(3H, s), 1.83–2.05(8H, m), 2.20–2.60(3H, m), 3.70–3.82(2H, m), 4.99–5.08(2H, m), 5.42–5.52(1H, m), 5.70–5.75(1H, m), 6.20–6.31(1H, m)

EXAMPLE 31

Disodium (E,E)-1-carboethoxy4,8,12-trimethyl-3,7,11-tridecatrienylphosphonate

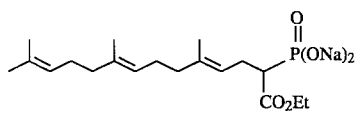

0.30 g of the diethyl (E,E)-1-carboethoxy-4,8,12-trimethyl- 3,7,11-tridecatrienylphosphonate prepared in Example 24 was dissolved in 10 ml of dichloromethane, followed by the addition thereto of 0.6 ml of 2,4,6-collidine and 0.6 ml of trimethylbromosilane. The obtained mixture was stirred at room temperature overnight, followed by the addition thereto of icewater. The resulting mixture was acidified with 2N hydrochloric acid and extracted with ethyl acetate. The organic layer was washed with a saturated aqueous solution of common salt, dried over anhydrous magnesium sulfate and distilled to remove the solvent. The obtained crude oil was purified by dissolving it in 1.8 ml of 1N aqueous sodium hydroxide and subjecting the obtained solution to CHP—20—P gel column chromatography (solvent: water/acetonitrile). 0.04 g of the title compound was obtained as a white solid.

¹H-NMR(D₂O); δ(ppm) 1.11(3H, t, J=6.5Hz), 1.47(3H, s), 1.48(3H, s) 1.52(3H, s), 1.55(3H, s), 1.84–2.02(8H, m), 2.18–2.28(1H, m), 2.46–2.58(2H, m), 3.97(2H, q, J=6.5Hz), 4.95–5.08(3H, m)

EXAMPLE 32

Trisodium salt of (E,E)-carboxy-4,8,12-trimethyl-3,7,11-tridecatrienylphosphonic acid

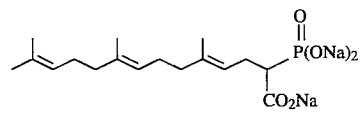

0.27 g of the crude oil prepared in Example 28, which mainly comprised disodium salt of ethyl (E,E)-1-carboxy-4,8,12-trlmethyl-3,7,11-tridecatrienylphosphonate, was dissolved in 10 ml of dichlcoromethane, followed by the addition thereto of 0.5 ml of collidine and 0.5 ml of trimethylbromosilane. The obtained mixture was stirred at room temperature overnight, followed by the addition thereto of ice-water. The resulting mixture was acidified with 2N hydrochloric acid and extracted with ethyl acetate. The organic layer was washed with a saturated aqueous solution of common salt, dried over anhydrous magnesium sulfate and distilled to remove the solvent. The obtained crude oil was purified by dissolving it in 3 ml of 1N aqueous sodium hydroxide and subjecting the solution to CHP—20—P gel column chromatography (solvent: water/acetoni- trile). 0.19 g of the title compound was obtained as a white solid.

¹H-NMR(D₂O); δ(ppm) 1.46(6H, s), 1.50(3H, s), 1.53(3H, s), 1.82–2.00(8H, m), 2.17–2.40(3H, m), 5.00–5.11(3H, m)

EXAMPLES 33 TO 35

The following compounds were prepared in a similar manner to that of the Example 32.

EXAMPLE 33

Trisodium salt of-(E,E)-1-carboxy-5,9,13-trimethyl-4,8,12-tetradecatrienylphosphonic acid

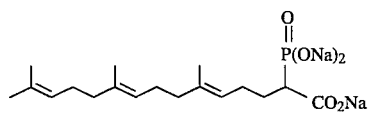

¹H-NMR(D₂O); δ(ppm) 1.47(9H, s), 1.53(3H, s), 1.60–2.02(12H, m), 2.31–2.41 ( m), 4.99–5.18(3H, m)

EXAMPLE 34

Trisodium salt of (E,E,E)-1-carboxy-6,10,14-trimethyl-3,5,9,13-pentadecatetraenylphosphonic acid

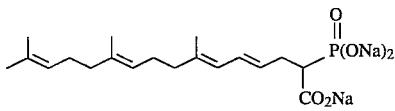

¹H-NMR(D₂O); δ(ppm) 1.45(6H, s), 1.54(3H, s), 1.58(3H, s), 1.83–2.06(8H, m), 2.20–2.45(3H, m), 4.98–5.10(2H, m), 5.40–5.54(1H, m), 5.70–5.76(1H, m), 6.18–6.29(1H, m)

EXAMPLE 35

Trisodium salt of 1-carboxy,4-{(E,E)-N-methyl-3,7,11-trimethyl-2,6,10-dodecatrienylamino}burylphosphonic acid

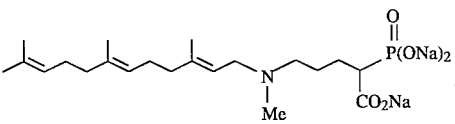

¹H-NMR(D₂O); δ(ppm) 1.20–1.38 (2H, m), 1.45(6H, s), 1.48(3H, s), 1.52(3H, s), 1.55–1.65(5H, m), 1.85–1.90(2H, m), 1.90–2.00 (3H, m), 2.01(3H, s), 2.22–2.38(3H, m), 2.88(2H, d, J=6Hz), 4.98–5.05(2H, m), 5.08–5.15(1H, m)

EXAMPLE 36

{(E,E)-3,7,11-Trimethyl-2,6,10-dodecatrienylamino}-amino}methylbis(phosphonic acid diethyl)

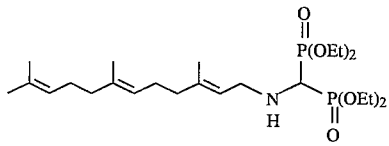

A mixture comprising 5 g of farnesylamine, 4.5 of ethyl orthoformate and 11.6 ml of diethyl phosphite was stirred it 150° C. for one hour, cooled and concentrated in a vacuum to remove unreacted ethyl orthoformate and diethyl phosphite. The residue was purified by silica gel column chromatography [solvent: methanol/dichloromethane (100 : 1)] to give 1.5 g of the title compound.

$^1$H-NMR(CDCl$_{13}$); δ(ppm) 1.33(12H, t), 1.60(6H, s), 1.66(3H, s), 1.68(3H, s), 2.05(8H, m), 3.30(1H, t), 3.47(2H, d), 4.22(8H, m), 5.10(2H, m), 5.22(1H, t)

EXAMPLE 37

{(E,E)-N-Methyl,3,7,11-trimethyl-2,6,10-dodecatrienylamino}methylbis(phosphonic acid diethyl)

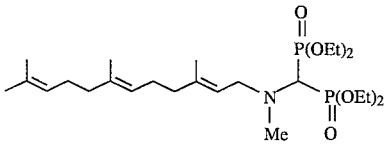

0.5 g of the {(E,E)-3,7,11-trimethyl-2,6,10-dodecatrienylamino}methylbis(phosphonic acid diethyl) prepared in the Example 36 was dissolved in 2 ml of dimethylformamide. 0.1 ml of methyl iodide was added to the obtained solution four times at intervals of one hour. The obtained mixture was stirred at room temperature for 12 hours and distilled in a vacuum to remove the solvent. The residue was purified by silica gel column chromatography [solvent: benzene/acetone (5 : 1)] to give 0.2 g of the title compound.

$^1$H-NMR(CDCl$_3$); δ(ppm) 1.34(12H, t), 1.60(6H, s), 1.68(6H, s), 2.05(8H, m), 2.68(3H, s), 3.40(2H, d), 3.40(1H, t), 4.20(8H, m), 5.10(2H, m), 5.19(1H, t)

EXAMPLES 38 TO 51

The following compounds were prepared in a similar manner to that of Examples 36 and 37.

EXAMPLE 38

4-{(E)-N-Methyl-3,7-dimethyl-2,6-octadienylamino}butyl- 1,1-bis(phosphonic acid diethyl)

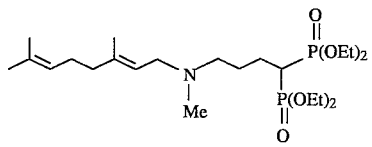

$^1$H-NMR(CDCl$_3$ ); δ(ppm) 1.32(12H, t, J=8Hz), 1.60(3H, s), 1.63(3H, s), 1.68(3H, s), 1.70–2.15(8H, m), 2.20(3H, s), 2.23–2.41 (3H, m), 2.94(2H, d, J=7Hz), 4.13–4.22(8H, m), 5.05–5.13(1H, m), 5.20–5.27(1H, m)

EXAMPLE 39

4{(E}-N-Ethyl-3,7-dimethyl-2,6-octadienylamino}butyl-1,1-bis(phosphonic acid diethyl)

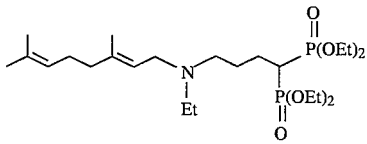

$^1$H-NMR(CDCl$_3$); δ(ppm) 1.05(3H, t, J=7Hz), 1.34(12H, t, J=8Hz), 1.60(3H, s), 1.65(6H, s), 1.66–1.75(4H, m), 1.90–1.98(2H, m), 2.00–2.15(4H, m), 2.22–2.40(1H, m), 2.41–2.58(2H, m), 3.02–3.15(2H, m), 5.05–5.10 (1H, m) , 5.21–5.29(1H, m)

EXAMPLE 40

4-{(E)-3,7,-Dimethyl-2,6,-octadienylamino}butyl-1,1-bis(phosphonic acid diethyl)

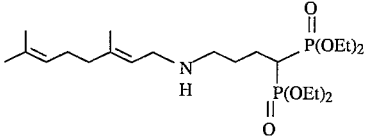

$^1$H-NMR(CDCl$_3$); δ(ppm) 1.32(12H, t, J=7Hz), 1.60(3H, s), 1.65(3H, s), 1.67(3H, s), 1.75–2.15(9H, m), 2.25–2.45(1H, m), 2.72(2H, t, J=6Hz), 3.35(2H, d, J=7Hz), 4.12–4.25(8H, m), 5.01–5.10(1H, m), 5.24–5.30(1H, m)

EXAMPLE 41

5-{(E)-N-Methyl-1,5,9-trimethyl-4,8-decadienyl-amino}pentyl- 1,1-bis(phosphonic acid diethyl)

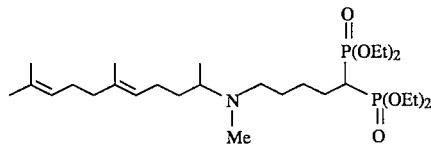

¹H-NMR(CDCl₃); δ(ppm) 1.05 (3H, d, J=6Hz ), 1.36(12H, t, J=7Hz), 1.50–1.77(8H, m), 1.60(6H, s), 1.70(3H, s), 1.84–2.13(10H, m), 2.15–2.38(3H, m), 4.13–4.26 (8H, m) , 5.07–5.15(2H, m)

EXAMPLE 42

Diethyl 1-carboethoxy-4-{(E)-N-methyl-1,5,9-trimethyl-4,8-decadienylamino}butylphosphonate

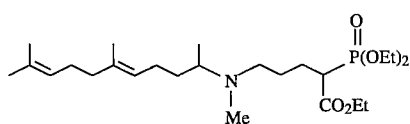

¹H-NMR(CDCl₃); δ(ppm) 0.95(3H, d, J=SHz), 1.20–1.38(9H, m), 1.41–1.67(12H, m), 1.70(3H, s), 1.78–1.93(2H, m), 1.95–2.02(3H, m), 2.02–2.05(2H, m), 2.20(3H, s), 2.30–2.50(2H, m), 2.92–3.04(1H, m ), 4.08–4.25(6H, m), 5.06–5.14(2H, m)

EXAMPLE 43

4-{(E)-N-Methyl-3,7-dimethyl-2,6-octadienyl-amino}butyl 1,1-bis(phosphonic acid disodium salt)

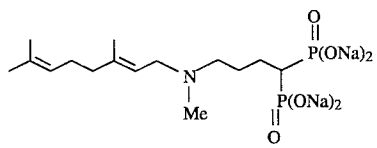

¹H-NMR(D₂O); δ(ppm) 1.46(3H, s), 1.50(3H, s), 1.52(3H, s), 1.53–1.68(4H, m), 1.95–2.05(5H, m), 2.15(3H, s), 2.38–2.45(2H, m), 3.03(2H, d, J=8Hz), 5.00–5.07(1H, m), 5.11–5.18(1H, m)

EXAMPLE 44

4-{(E)-N-Ethyl-3,7-dimethyl-2,6-octadienylamino}butyl-1,1-bis(phosphoric acid disodium salt)

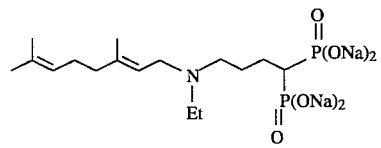

¹H-NMR(D₂O); δ(ppm) 0.94(3H, t, J=7Hz ), 1.46(3H, s), 1.52(6H, s), 1.57–1.70(5H, m), 1.96–2.08(4H, m), 2.50–2.67(4H, m), 3.20(2H, d, J=8Hz), 5.00–5.07(1H, m), 5.12–5.18(1H, m)

EXAMPLE 45

4-{(E)-3,7-Dimethyl-2,6-octadienylamino}butyl-1,1-bis(phosphonic acid disodium salt)

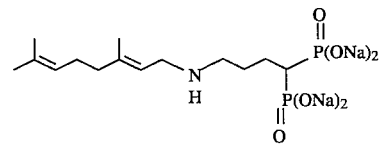

¹H-NMR(D₂O); δ(ppm) 1.45(3H, s), 1.52(3H, s), 1.55(3H, s), 1.58–1.80(5H, m), 1.92–2.05(4H, m), 2.75–2.85(2H, m), 3.38(2H, d, J=8Hz), 5.00–5.08(1H, m), 5.10–5.17(1H, m)

EXAMPLE 46

5-{(E}-N-Methyl-1,5,9-trimethyl-4,8-decadienyl-amino}-pentyl- 1,1-bis(phosphonic acid disodium salt)

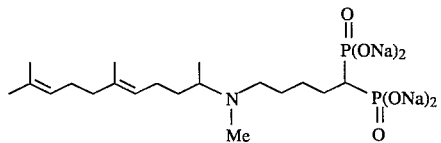

¹H-NMR(D₂O); δ(ppm) 0.95(3H, d, J=6Hz), 1.32–1.46(4H, m), 1.51(6H, s), 1.58(3H, s), 1.47–1.70(4H, m), 1.81–1.96(4H, m), 1.96–2.10(3H, m), 2.16(3H, s), 2.44–2.52(2H, m), 2.64(1H, m), 5.04–5.13(2H, m)

EXAMPLE 47

{(E,E)-3,7,11-Trimethyl-2,6,10-dodecatrienylamino}-methylbis(phosphonic acid sodium salt)

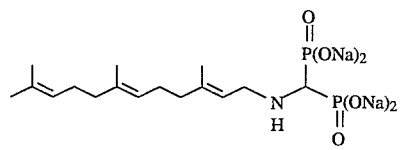

$^1$H-NMR(D$_2$O); δ(ppm) 1.47(6H, s), 1.54(3H, s), 1.62(3H, s), 1.89(2H, m), 1.98(6H, m), 2.88(1H, 3.81(2H, d), 5.05(2H, m), 5.25(1H, t)

EXAMPLE 48

{(E,E)-N-Methyl-3,7,11-trimethyl-2,6,10-dodecatrienylamino}methylbis(phosphonic acid disodium salt)

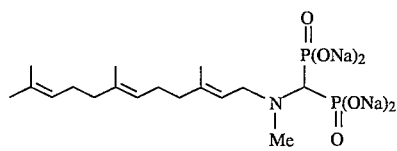

$^1$H-NMR(D$_2$O); δ(ppm) 1.48(6H, s), 1.54(3H, s), 1.64(3H, s), 1.88(2H, m), 1.95(2H, m), 2.03(4H, t), 2.89(3H, s), 3.13(2[H, t), 3.98(2H, d), 5.05(2H, m), 5.20(1H, t)

EXAMPLE 49

5-{(E,E)-N-Methyl-3,7,11-trimethyl-2,6,10-dodecatrienylamino}pentyl- 1,1-bis(phosphonic acid disodium salt)

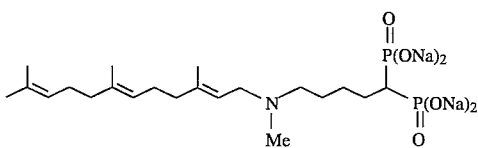

$^1$H-NMR(D$_2$O); δ(ppm) 1.32–1.75 (7H, m), 1.48(6H, s), 1.52(3H, s), 1.55(3H, s), 1.85–2.15(8H, m), 2.07(3H, s), 2.32–2.40 (2H, m), 2.95(2H, d, J=7Hz), 5.01–5.12(2H, m), 5.14–5.18(1H, m)

EXAMPLE 50

Disodium 1-carboethoxy-4-{(E)-N-methyl-1,5,9-trimethyl-4,8-decadienylamino}butylphosphonate

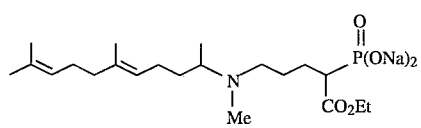

$^1$H-NMR(D$_2$O); δ(ppm) 1.07(3H, d, J=6Hz), 1.12(3H, t, J=7Hz), 1.31–1.40(2H, m), 1.45(3H, s), 1.46(3H, s), 1.50(3H, s), 1.51–1.72(4H, m), 1.73–1.91(4H, m), 1.93–2.00(2H, m), 2.44(3H, s), 2.45–2.59(1H, m), 2.74–2.86(2H, m), 3.95–4.07(3H, m), 4.95–5.03(2H, m)

EXAMPLE 51

Trisodium salt of 1-carboxy-4,{(E)-N-methyl-1,5,9-trimethyl-4,8-decadienylamino}butylphosphonic acid

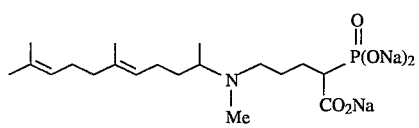

$^1$H-NMR(D$_2$O); δ(ppm) 0.90(3H, d, J=8Hz), 1.18–1.38(4H, m), 1.47(6H, s), 1.53(3H, s), 1.57–1.70(2H, m), 1.80–1.94(4H, m), 1.95–2.02(2H, m), 2.07(3H, s), 2.30–2.42(3H, m), 2.35–2.62(1H, m), 5.01–5.10 (2H, m)

EXAMPLE 52

4-{(E,E)-N-Methyl-3-methyl-7-phenyl-2,6-octadienylamino}butyl- 1,1-bis(phosphonic acid diethyl)

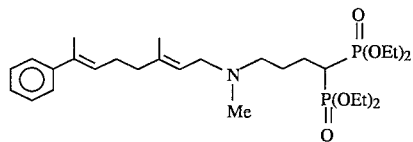

A mixture comprising 0.5 g of (E)-N-methyl-3,7-dimethyl- 7-phenyl-2,6-heptadienylamine, 1.2 g of the 4-p-tolylsulfuryloxybutyl-1,1-bis(phosphonic acid diethyl) prepared in the Preparative Example 9, 0.32 g of potassium carbonate and 7 ml of N,N-dimethylformamide was stirred at room temperature for 12 hours, followed by the addition thereto of water. The resulting mixture was extracted with ethyl acetate. The organic layer was washed with a saturated aqueous solution of common salt, dried over anhydrous magnesium sulfate and distilled to remove the solvent. The obtained crude product was purified by silica gel column chromatography to give 0.79 g of the title compound.

EXAMPLES 53 TO 55

The following compounds were prepared in a similar manner to that of Example 52.

EXAMPLE 53

4-{(E)-N-Methyl-3,7-dimethyl-2,6-octadienylamino}-butyl 1,1-bis(phosphoninc acid diethyl)

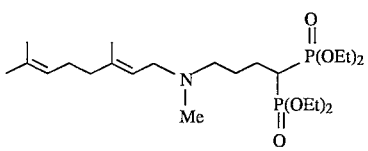

$^1$H-NMR(CDCl$_3$); δ(ppm) 1.32(12H, t, J=8Hz), 1.60(3H, s), 1.63(3H, s), 1.68(3H, s), 1.70–2.15(8H, m), 2.20(3H, s), 2.23–2.41(3H, m), 2.94(2H, d, J=7Hz), 4.13–4.22(8H, m), 5.05–5.13(1H, m), 5.20–5.27(1H, m)

EXAMPLE 54

4-{(E)-N-Ethyl-3,7-dimethyl-2,6-octadienylamino}butyl- 1,1-bis(phosphonic acid diethyl)

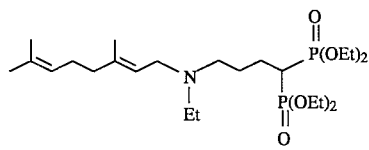

$^1$H-NMR(CDCl$_3$); δ(ppm) 1.05(3H, t, J=7Hz ), 1.34 ( 12H, t, J=8Hz), 1.60(3H, s), 1.65(6H, s), 1.66–1.75(4H, m), 1.90–1.98 (2H, m), 2.00–2.15(4H, m), 2.22–2.40 (1H, m), 2.41–2.58 ( 2H, m), 3.02–3.15 (2H, m), 5.05–5.10 (1H, m), 5.21–5.29 (1H, m)

EXAMPLE 55

5-{(E)-N-Methyl-1,5,9-trimethyl-4,8-decadienyl-amino}pentyl- 1,1-bis(phosphonic acid diethyl)

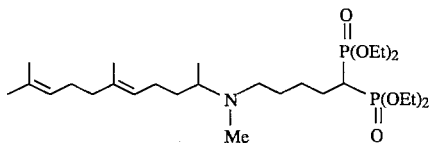

$^1$H-NMR(CDCl$_3$ ); δ(ppm) 1.05 (3H, d, J=6Hz), 1.36 (12H, t, J=7Hz), 1.50–1.77(8H, m), 1.60(6H, s), 1.70(3H, s), 1.84–2.13(10H, m), 2.15–2.38(3H, m), 4.13–4.26(8H, m), 5.07–5.15(2H, m)

We claim:

1. A phosphorus-containing isoprenoid derivative represented by the following general formula (I) or a pharmacologically acceptable salt thereof:

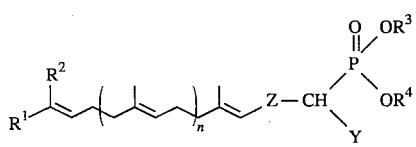

wherein $R^1$ and $R^2$ may be the same or different from each other and are each selected from the group consisting of a hydrogen atom, a lower alkyl group, a cycloalkyl group, an alkenyl group, an alkynyl group, an aryl group which may be substituted, an arylalkyl group in which the aryl group may be substituted, a heteroaryl group and a heteroarylalkyl group;

$R^3$ and $R^4$ may be the same or different from each other and each are selected from the group consisting of a hydrogen atom, a lower alkyl group and an alkali metal;

Y is selected from the group consisting of

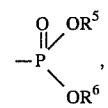

wherein $R^5$ and $R^6$ may be the same or different from each other and each are selected from the group consisting of a hydrogen atom, a lower alkyl group and an alkali metal and —CO$_2$R$^7$, wherein $R^7$ is selected from the group consisting of a hydrogen atom, a lower alkyl group and an alkali metal;

Z is

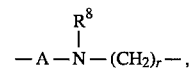

wherein $R^8$ is selected from the group consisting of a hydrogen atom and a lower alkyl group; A is an alkylene chain having 1 to 5 carbon atoms and which may have a substituent on each carbon; and r is zero or an integer of 1 to 5; and n is zero or an integer of 1 to 5.

2. A drug composition comprising a pharmacologically effective amount of the phosphorus-containing isoprenoid derivative, or pharmacologically acceptable salt thereof, as set forth in claim 1, and a pharmacologically acceptable carrier.

3. A method of treating a disease for which a squalene synthetase inhibiting action is efficacious, comprising the step of administering a pharmaceutically effective amount of the phosphorus-containing isoprenoid derivative, or pharmacologically acceptable salt thereof, as set forth in claim 1 to a subject afflicted with said disease.

4. A method of treating hyperlipemia, comprising the step of administering a pharmaceutically effective amount of the phosphorus-containing isoprenoid derivative, or pharmacologically acceptable salt thereof, as set forth in claim 1 to a subject afflicted with said disease.

5. A phosphorus-containing isoprenoid derivative represented by the following general formula (I), or a pharmacologically acceptable salt thereof:

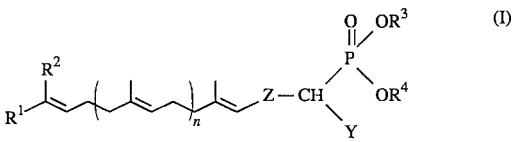

wherein $R^1$ and $R^2$ may be the same or different from each other and are each selected from the group consisting of a hydrogen atom, a lower alkyl group, a cycloalkyl group, an alkenyl group, an alkynyl group, an aryl group which may be substituted, an arylalkyl group in which the aryl group may be substituted, a heteroaryl group and a heteroarylalkyl group;

$R^3$ and $R^4$ may be the same or different from each other and each are selected from the group consisting of a hydrogen atom, a lower alkyl group and an alkali metal;

Y is —CO$_2$R$^7$, wherein $R^7$ is selected from the group consisting of a hydrogen atom, a lower alkyl group and an alkali metal;

Z is selected from the group consisting —CH$_2$)$_m$— wherein m is zero or an integer of 1 to 3, —(CH$_2$)$_p$— CH=CH—(CH$_2$)$_q$— wherein p is 0 or 1 and q is 1 or 2 and

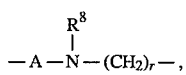

wherein $R^8$ is selected from the group consisting of a hydrogen atom and a lower alkyl group, A is an alkylene chain which has 1 to 5 carbon atoms and which may have a substituent on each carbon and r is zero or an integer of 1 to 5; and n is zero or an integer of 1 to 5.

6. A drug composition comprising a pharmacologically effective amount of the phosphoruscontaining isoprenoid derivative, or pharmacologically acceptable salt thereof, as set forth in claim 5, and a pharmacologically acceptable carrier.

7. A method of treating a disease for which a squalene synthetase inhibiting action is efficacious, comprising the step of administering a pharmaceutically effective amount of the phosphorus-containing isoprenoid derivative, or pharmacologically acceptable salt thereof, as set forth in claim 5 to a subject afflicted with said disease.

8. A method of treating hyperlipemia, comprising the step of administering a pharmaceutically effective amount of the phosphorus-containing isoprenoid derivative, or pharmacologically acceptable salt thereof, as set forth in claim 5 to a subject afflicted with said disease.

* * * * *

UNITED STATES PATENT AND TRADEMARK OFFICE
CERTIFICATE OF CORRECTION

PATENT NO. : 5,453,524
DATED : September 26, 1995
INVENTOR(S) : Katsuya Tagami et al It is certified that error appears in the above-indentified patent and that said Letters Patent is hereby corrected as shown below:

IN THE ABSTRACT line 20; change "Formula" to ---formula---.
line 23; change "Formula" to ---formula---.

Col. 41, line 47; after "(I)" insert a comma ---,---.

Col. 43, line 15; change "phosphoruscontaining" to --phosphorus-containing--.

Signed and Sealed this

Ninth Day of July, 1996

BRUCE LEHMAN

Attest:

Attesting Officer

Commissioner of Patents and Trademarks